United States Patent
Kirschman

(10) Patent No.: US 10,285,770 B2
(45) Date of Patent: May 14, 2019

(54) BONE PLATING SYSTEM AND IMPLANT CARD HAVING AT LEAST ONE OR A PLURALITY OF PLATES

(71) Applicant: David Louis Kirschman, Dayton, OH (US)

(72) Inventor: David Louis Kirschman, Dayton, OH (US)

(73) Assignee: David Louis Kirschman, Dayton, OH (US)

(*) Notice: Subject to any disclaimer, the term of this patent is extended or adjusted under 35 U.S.C. 154(b) by 449 days.

(21) Appl. No.: 15/049,642

(22) Filed: Feb. 22, 2016

(65) Prior Publication Data

US 2016/0242863 A1    Aug. 25, 2016

Related U.S. Application Data

(60) Provisional application No. 62/120,089, filed on Feb. 24, 2015.

(51) Int. Cl.
| | | |
|---|---|---|
| *A61B 50/30* | (2016.01) | |
| *A61B 17/80* | (2006.01) | |
| *A61B 50/20* | (2016.01) | |
| *A61B 17/00* | (2006.01) | |
| *A61B 90/00* | (2016.01) | |

(52) U.S. Cl.
CPC ............. *A61B 50/30* (2016.02); *A61B 17/80* (2013.01); *A61B 17/808* (2013.01); *A61B 17/8061* (2013.01); *A61B 17/8085* (2013.01); *A61B 50/20* (2016.02); *A61B 2017/00526* (2013.01); *A61B 2050/3008* (2016.02);

(Continued)

(58) Field of Classification Search
CPC .......... A61B 2017/00526; A61B 17/80; A61B 17/8061; A61B 17/808; A61B 17/8085; A61B 17/8872; A61B 2090/037; A61B 2050/3008

See application file for complete search history.

(56) References Cited

U.S. PATENT DOCUMENTS

| 4,503,848 A | 3/1985 | Caspar et al. |
|---|---|---|
| 4,923,471 A | 5/1990 | Morgan |

(Continued)

FOREIGN PATENT DOCUMENTS

| WO | 2014089285 A1 | 6/2014 | |
|---|---|---|---|
| WO | WO 2014089285 A1 * | 6/2014 | ............. A61B 17/80 |

*Primary Examiner* — Christopher Beccia
(74) *Attorney, Agent, or Firm* — Jacox, Meckstroth & Jenkins

(57) ABSTRACT

A bone plating system and implant card having at least one or a plurality of plates. The bone plating system and implant card has a card member or support having the at least one or a plurality of plates that are integrally, monolithically, or otherwise formed in or adhered to the card member so that the at least one or plurality of plates can be detached or removed from the card member manually or with a cutting instrument or tool. In one illustrative embodiment, the card member comprises a plurality of different plates that are the necessary plates for a single surgical procedure, such as a craniotomy. The bone plating system or implant card allows for selection of plates of varying sizes, shapes and configurations in a single card member, which could be generally planar or could also be non-planar or lie in a plane that is not flat.

33 Claims, 5 Drawing Sheets

(52) U.S. Cl.
CPC ... *A61B 2090/037* (2016.02); *A61B 2090/061* (2016.02); *A61B 2090/3937* (2016.02)

(56) References Cited

U.S. PATENT DOCUMENTS

| | | | | |
|---|---|---|---|---|
| 4,959,065 A * | 9/1990 | Arnett | ................ | A61B 17/8085 |
| | | | | 606/285 |
| 5,201,737 A | 4/1993 | Leibinger et al. | | |
| 5,578,036 A | 11/1996 | Stone et al. | | |
| 5,690,631 A * | 11/1997 | Duncan | .............. | A61B 17/8085 |
| | | | | 606/281 |
| 6,193,721 B1 * | 2/2001 | Michelson | ......... | A61B 17/1604 |
| | | | | 606/246 |
| 7,717,946 B2 * | 5/2010 | von Oepen | ........ | A61B 17/8085 |
| | | | | 264/323 |
| 8,709,054 B2 * | 4/2014 | Lowry | ............... | A61B 17/1671 |
| | | | | 606/295 |
| 8,784,456 B2 | 7/2014 | Longepied | | |
| 8,961,517 B2 | 2/2015 | McClintock et al. | | |
| 9,023,085 B2 | 5/2015 | Strippgen | | |
| 2005/0216008 A1 * | 9/2005 | Zwirnmann | ........... | A61B 17/68 |
| | | | | 606/281 |
| 2011/0301609 A1 | 12/2011 | Longepied | | |
| 2014/0128873 A1 | 5/2014 | McClintock et al. | | |
| 2015/0018829 A1 | 1/2015 | Woodburn, Sr. et al. | | |
| 2015/0018830 A1 | 1/2015 | Knoepfle et al. | | |
| 2015/0313652 A1 | 11/2015 | Burckhardt et al. | | |

\* cited by examiner

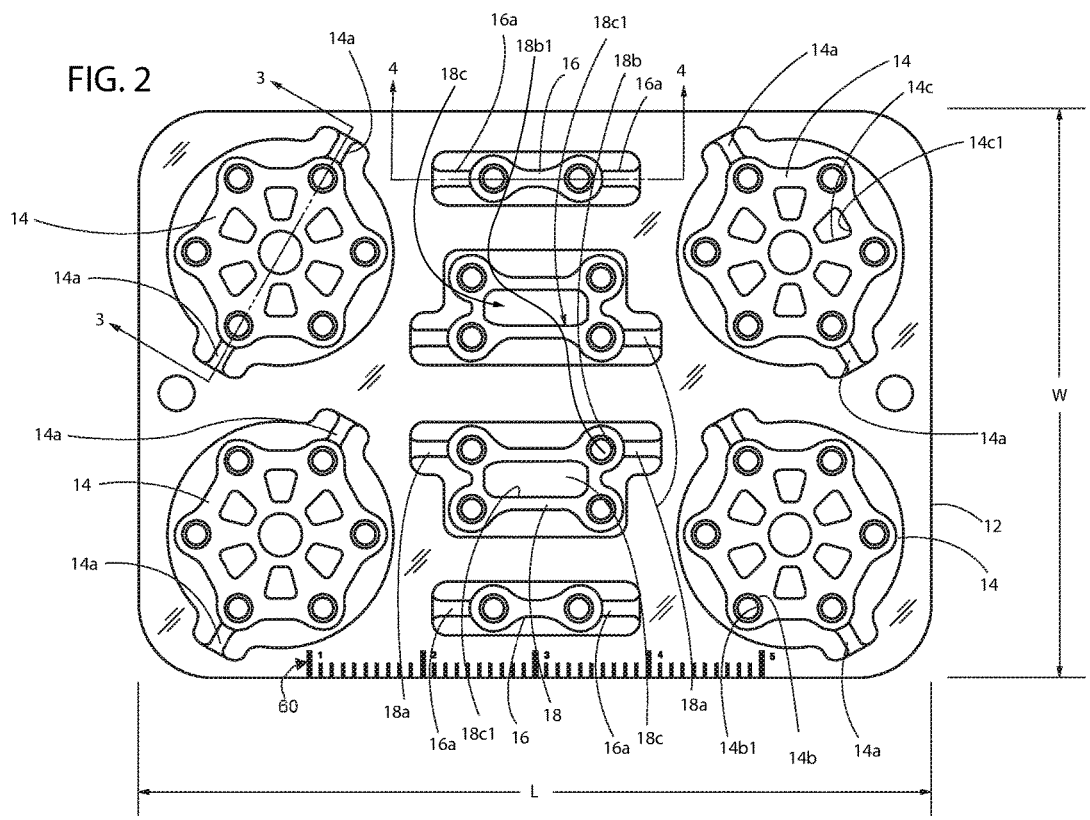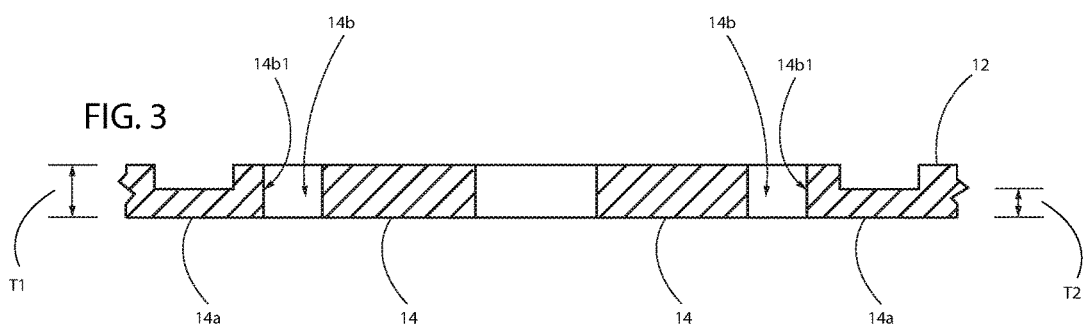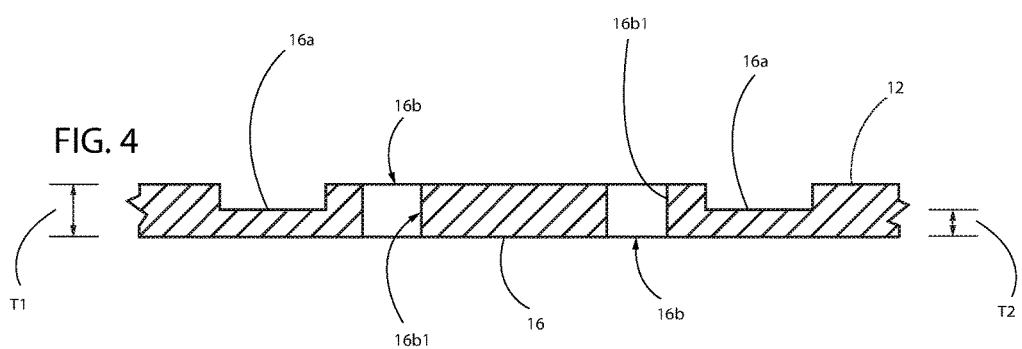

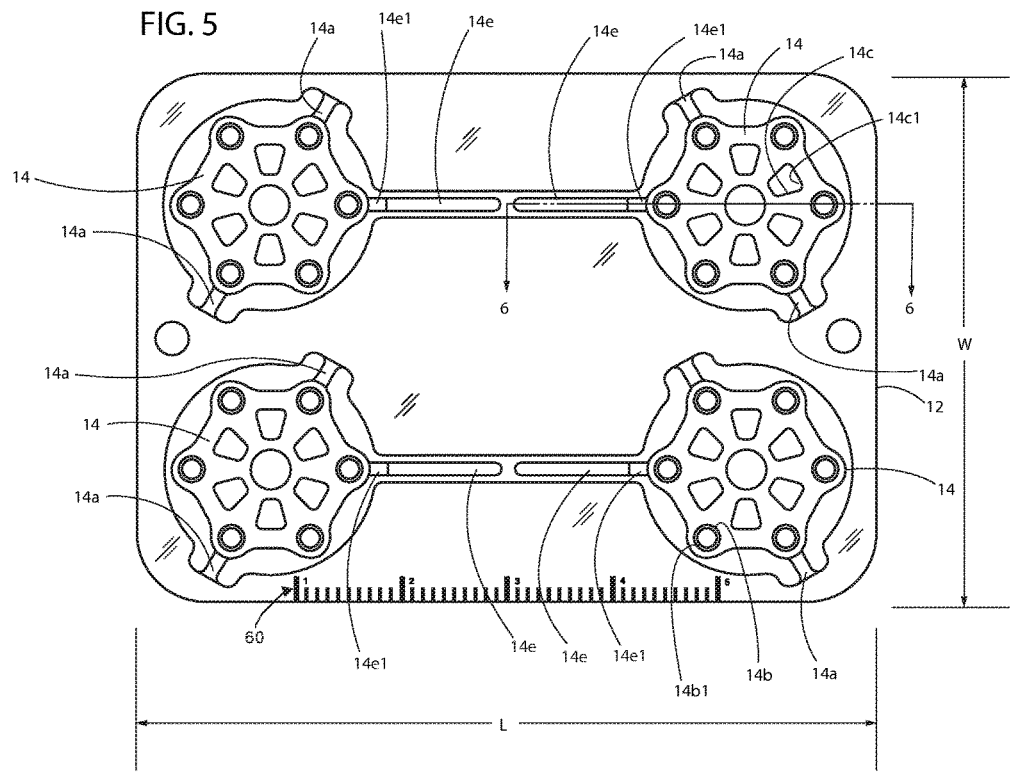
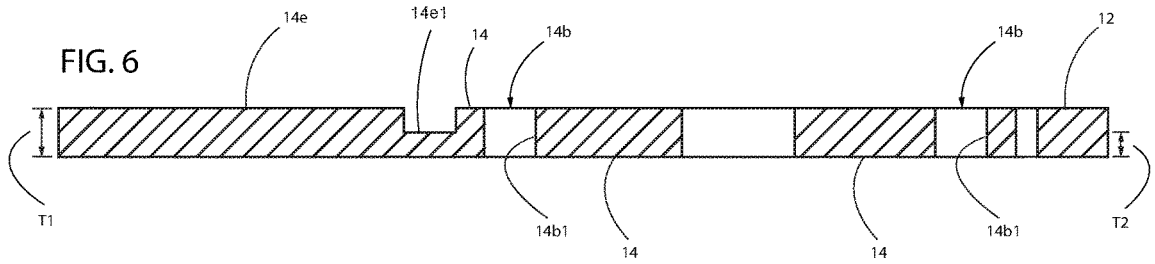

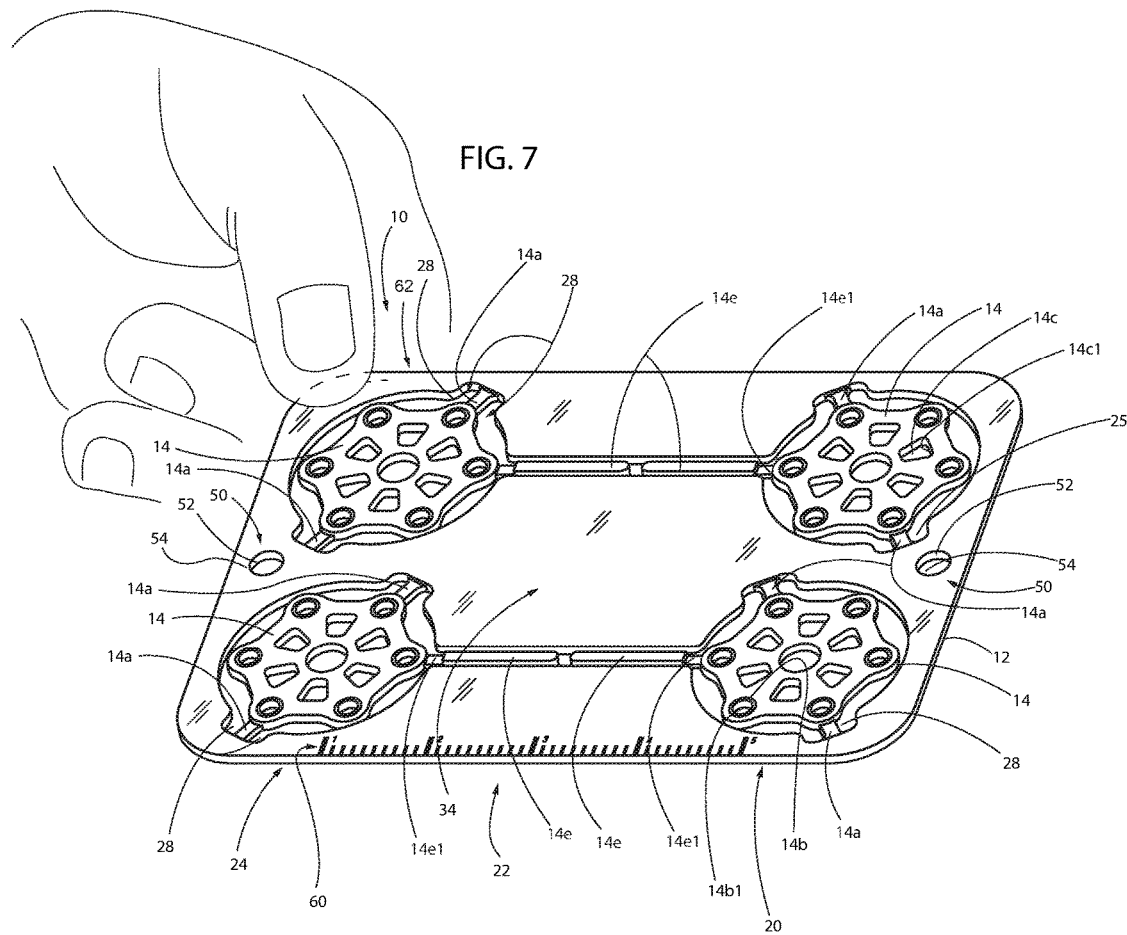

BONE PLATING SYSTEM AND IMPLANT CARD HAVING AT LEAST ONE OR A PLURALITY OF PLATES

CROSS-REFERENCE TO RELATED APPLICATION

The present application claims priority to provisional U.S. application Ser. No. 62/120,089 filed Feb. 24, 2015, to which Applicant claims the benefit of the earlier filing date. This provisional application is incorporated herein by reference and made a part hereof.

BACKGROUND OF THE INVENTION

1. Field of the Invention

This invention relates to a bone plating system and/or implant card having at least one or a plurality of plates.

2. Description of the Related Art

Various plates have long been used for the fixation of cranial and other boned following surgery or fracture. Exemplary examples include U.S. Pat. Nos. 5,201,737; 5,578,036 and 4,503,848. Plates are commonly provided in multi-component kits comprising plates of various sizes and shapes to conform to the specific anatomical or patho-anatomical need.

Recently, there has been increasing emphasis on the costs of providing such kits to hospitals. Additionally, there are cost and safety concerns about the need to re-sterilize kits. Finally, there is a need to consistently re-inventory partially used kits which requires significant labor.

What is needed, therefore, is a convenient, inexpensive, single use kit or system containing the basic plating components needed for a specific surgical procedure, such as a craniotomy procedure.

It is therefore desired to provide a bone plating system and implant card that overcomes one or more of the problems in the prior art.

SUMMARY OF THE INVENTION

Advantageously, a system and implant card of bone plates for cranial or other bone fixation manufactured on a single, integral monolithic metallic or polymeric implant card is provided. The system and implant card allows for a selection of at least one or a plurality of plates of varying sizes and configurations in a single construct and further allows plates to be selectively removed intraoperatively or even before a surgical procedure. The plates being integrally attached to the implant card via thin webs which can easily be detached or cut as needed during a surgical procedure.

In one embodiment, a generally flat or planar plate or card comprises an implant-grade medical material. This material can be metallic, such as titanium or polymeric such as polyether ether ketone (PEEK). In one embodiment, the system or implant card has at least one or a plurality of integrally manufactured or molded bone plates of varying shapes and sizes. Examples include round burr-hole cover type plates, linear, X-shaped, or quadrangular plates.

The at least one or a plurality of plates are integrally manufactured or formed into the implant card using machining, molding, etching, additive manufacturing, cutting or other techniques as appropriate. The at least one or a plurality of plates are connected to the implant card via thin webs of material, such that they are stable for handling, but can easily be removed manually or using a simple wire-cutter-type instrument. Specific recesses are provided in the implant card at the point the web interfaces with the implant card to allow for the ingress of a cutting instrument. The implant card may further optionally comprise ruler indicia, alignment holes for manufacturing, screw holes or other features.

In another embodiment, the at least one or a plurality of plates may further comprise integral placement handles, which themselves have a web connection which can easily be cut or broken off at the time of implantation.

An object of the invention is to provide a bone plating system and implant card that is easy to manufacture and permits a selection of plates of varying sizes and configurations in a single construct.

Another object of the invention is to provide a bone plating system and implant card in a single, integral or even monolithic construction.

Still another object of the invention is to provide a bone plating system and implant card that is easy to manufacture using conventional manufacturing techniques, such as machining, etching, molding or other similar processes.

Yet another object of the invention is to provide a bone plating system and implant card that is integrally or monolithically formed in a card member that has at least one or a plurality of plates that may be the same or different.

Another object of the invention is to provide a bone plating system and implant card that comprises a plurality of plates that are the same shape and size.

Another object of the invention is to provide a bone plating system and implant card that comprises a plurality of plates that have at least one of a different size, a different shape or a different configuration.

Another object of the invention is to provide a bone plating system and implant card having a plurality of plates coupled to, integrally formed or monolithically formed in the card member using at least one or a plurality of webs that can be detached, broken or cut so that the plurality of plates are permitted to be selectively and detachably removed from the card member.

Another object of the invention is to provide a bone plating system and implant card that can be manually held so that at least one of the plurality of plates can be positioned in a desired position relative to bone. In other words, the implant card may be utilized as a support for supporting one or more plates in a desired position so that it can be secured to bone.

Another object of the invention is to provide at least one or a plurality of recesses associated with at least one or a plurality of webs to enable easy access to the at least one or a plurality of webs to permit the ingress of a cutting tool or instrument.

Yet another object of the embodiments being described is to provide a bone plating system and implant card having all the plates necessary to perform a particular surgical procedure, such as a craniotomy procedure.

Another object of the invention is to provide a bone plating system and implant card wherein the at least one or a plurality of plates comprises an integral placement handle used to allow positioning of a plate and that can be separated from the plate at the time of implantation.

Another object of the invention is to provide a bone plating system and implant card that has one or more features adapted to assist the surgeon during a surgical procedure. For example, the bone plating system and implant card may comprise indicia, such as a ruler indicia, aligning mechanisms, such as holes, or other features integrally or monolithically provided or situated on the implant card.

In one aspect, one embodiment comprises a bone plating system comprising a card member, the card member having at least one plate integrally manufactured in or monolithically formed in the card member.

In another aspect, another embodiment comprises an implant card comprising a card member, the card member comprising a plurality of plates adapted to be detached or removed from the card member for use on a patient.

This invention, including all embodiments shown and described herein, could be used alone or together and/or in combination with one or more of the features covered by one or more of the following list of features:

The bone plating system or implant card wherein the card member is generally planar.

The bone plating system or implant card wherein the card member comprises a plurality of plate members integrally manufactured in or monolithically formed in the card member.

The bone plating system or implant card wherein the card member comprises a plurality of plate members that are each at least one of a different shape or a different size.

The bone plating system or implant card wherein the card member comprises a generally planar support, the plurality of plate members each being coupled to the planar support via at least one web that is adapted to permit a user to selectively remove at least one of the plurality of plate members from the planar support.

The bone plating system or implant card wherein the plurality of plate members being coupled to the planar support via a plurality of webs that are adapted to permit a user to selectively remove at least one of the plurality of plate members from the planar support.

The bone plating system or implant card wherein the plurality of plate members each comprise a plurality of screw holes adapted to receive a bone screw.

The bone plating system or implant card wherein each of the plurality of webs has a thickness that is less than a thickness of the planar support to facilitate a user removing the at least one of the plurality of plate members from the planar support The bone plating system or implant card wherein each of the planar support comprises a plurality of recesses associated with the plurality of webs, respectively, the plurality of recesses being adapted and sized to permit ingress of a cutting instrument used for cutting the plurality of webs.

The bone plating system or implant card wherein at least one of the plurality of plate members comprises at least one integral placement handle.

The bone plating system or implant card wherein the card member has a holding area adapted to permit a user to position or align at least one of the plurality of plate members during a surgical operation.

The bone plating system or implant card wherein the card member has a holding area adapted to permit a user to position or align at least one of the plurality of plate members during a surgical operation and prior to the at least one of the plurality of plate members being separated from the card member.

The bone plating system or implant card wherein the card member is a generally planar and metallic, the plurality of plate members are provided in the card member by at least one of machining, etching, or cutting.

The bone plating system or implant card wherein the card member is made of a molded polymer material, the plurality of plate members being molded in the card member.

The bone plating system or implant card wherein the card member comprises an indicia.

The bone plating system or implant card herein the indicia comprises a ruler indicia.

The bone plating system or implant card wherein the card member comprises at least one aligner for aligning the card member during a processing operation.

The bone plating system or implant card wherein the at least one aligner comprises a plurality of alignment apertures.

The bone plating system or implant card wherein the card member comprises a plurality of edges that cooperate to define an interior area in the card member, the plurality of plate members being generally located in the interior area.

The bone plating system or implant card wherein the plurality of plate members in the card member are made by a single processing operation.

The bone plating system or implant card wherein the card member is less than about ⅛ inch thick.

The bone plating system or implant card wherein the card member comprises a length less than about 4 inches a width less than about 3 inches and a thickness of less than about ⅛ inch.

The bone plating system or implant card wherein the card member and the plurality of plates are a single, integral or monolithic construction.

The bone plating system or implant card wherein the card member is metallic or polymeric and adapted to allow a selection of at least one of the plurality of plates to be selectively removed either before or during a surgical procedure.

The bone plating system or implant card wherein the card member comprises a support member, the plurality of plates are integrally or monolithically attached to the support member using at least one web.

The bone plating system or implant card wherein the at least one web comprises a thickness that is less than the support member.

The bone plating system or implant card wherein the card member comprises recesses generally located at a point or intersection where the at least one web interfaces the card member to permit ingress of a cutting tool.

The bone plating system or implant card wherein at least one of the plurality of plates has a shape or size that is different from another of the plurality of plates.

The bone plating system or implant card wherein the plurality of plates comprises at least one first group of plates and at least one second group of plates, the at least one first group of plates comprises a size or shape that is different from the at least one second group of plates.

The bone plating system or implant card wherein the plurality of plates can be separately or independently removed from the card member manually or with a hand tool.

The bone plating system or implant card wherein the card member has at least one aligner adapted to facilitate manufacturing, machining or processing the card member.

The bone plating system or implant card wherein the at least one aligner comprises a plurality of holes.

The bone plating system or implant card wherein the card member comprises a ruler indicia.

The bone plating system or implant card wherein the card member comprises a holding area for allowing a user to hold the card substantially simultaneously when at least one of the plurality of plates is being mounted to bone.

The bone plating system or implant card wherein at least one of the plurality of plates comprises an integral placement handle adapted for use during a surgical procedure and that can be separated from the at least one of the plurality of plates.

These and other objects and advantages of the invention will be apparent from the following description, the accompanying drawings and the appended claims.

BRIEF DESCRIPTION OF THE ACCOMPANYING DRAWINGS

FIG. 2 is a plan view of the bone plating system and implant card shown in FIG. 1;

FIG. 3 is a sectional view taken along the line 3-3 in FIG. 2;

FIG. 4 is another sectional view taken along the line 4-4 in FIG. 2;

FIG. 5 is a plan view of another embodiment of the invention, illustrating at least one or a plurality of plates having at least one integral placement handle;

FIG. 6 is a sectional view taken along the line 6-6 in FIG. 5 illustrating the at least one web for detachably securing or monolithically forming the integral placement handle with the at least one plate;

FIG. 7 is perspective view of the plate shown in FIGS. 5 and 6; AND

DETAILED DESCRIPTION OF THE PREFERRED EMBODIMENTS

Figure 1:
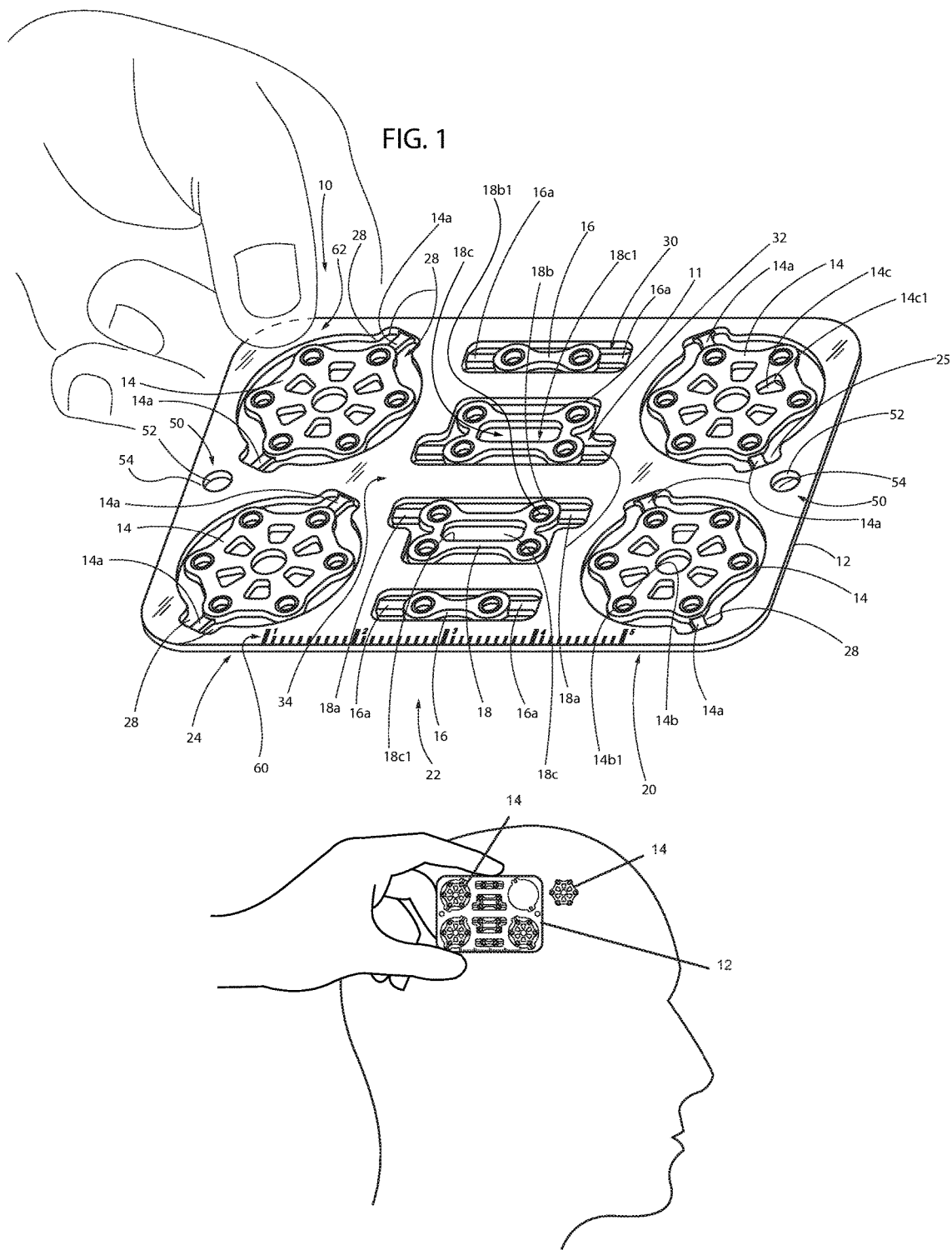
FIG. 1 is a perspective view of a bone plating system and implant card in accordance with one embodiment of the invention.

Referring now to FIG. 1, a bone plating system or implant card 10 is shown. The bone plating system or implant card 10 comprises a card member 12 that comprises and supports at least one or a plurality of plates 14, 16 and 18. The card member 12 is generally flat or planar in this embodiment, but as mentioned later, it could comprise a non-planar shape so that it is easily adapted to the anatomical environment in which it is used. The at least one or plurality of plates 14, 16 and 18 may be the same or, preferably, they may be of different shapes, sizes or configurations. One advantageous feature is that one or more of the bone plating systems or implant cards 10 can contain some or all of the implant components that are necessary for a surgical procedure.

In the illustration being described, the at least one or plurality of plates 14, 16 and 18 may be integrally provided in a plurality of groups 20, 22 and 26 in or on the card member 12. Note that within each group 20, 22 and 24, there may be at least one or plurality of the plates 14, 16 and 18. Within each group 20, 22 and 24, the at least one or plurality of plates 14, 16 and 18 may be the same or may be different. In the illustration being shown in FIG. 1, the at least one or plurality of plates 14 within groups 20 and 24 are the same, whereas the at least one or plurality of plates 16 and 18 in group 22 are of different sizes, shapes and configurations as shown.

In the illustration being described, the card member 12 and the at least one or plurality of plates 14, 16 and 18 may include a rounded burr hole cover type plate, a linear plate, an X-shaped plate, a circular plate, a quadrangular plate or any other plate component that may be necessary during a particular surgical procedure, such as a craniotomy procedure. The at least one or plurality of plates 14, 16 and 18 can be used during a surgical procedure, such as during a cranial procedure or a procedure involving the fixation of bone during or following surgery or following a fracture, for example. The at least one or plurality of plates 14, 16 and 18 can be separated manually or cut with an instrument or tool, as described later, before or during a surgical procedure.

Note that the card member 12 is generally planar as mentioned and provided in the shape and/or size of a conventional financial credit card (not shown). In the illustration being described, the card member 12 may comprise a length L (FIG. 2) that is less than about 4 inches, width W that is less than about 3 inches and thickness T1 (FIG. 3) that is less than ⅛ inch. In the illustration being described, the at least one or plurality of plates 14, 16 and 18 are integrally attached, affixed, monolithically molded or formed, machined or etched in the card member 12. Referring to FIGS. 1 and 2, the at least one or plurality of plates 14, 16 and 18 are defined by a plurality of cut-out, etched-out, recessed or open areas 28, 30 and 32, such as may result from a molding process, as shown.

Figure 8:
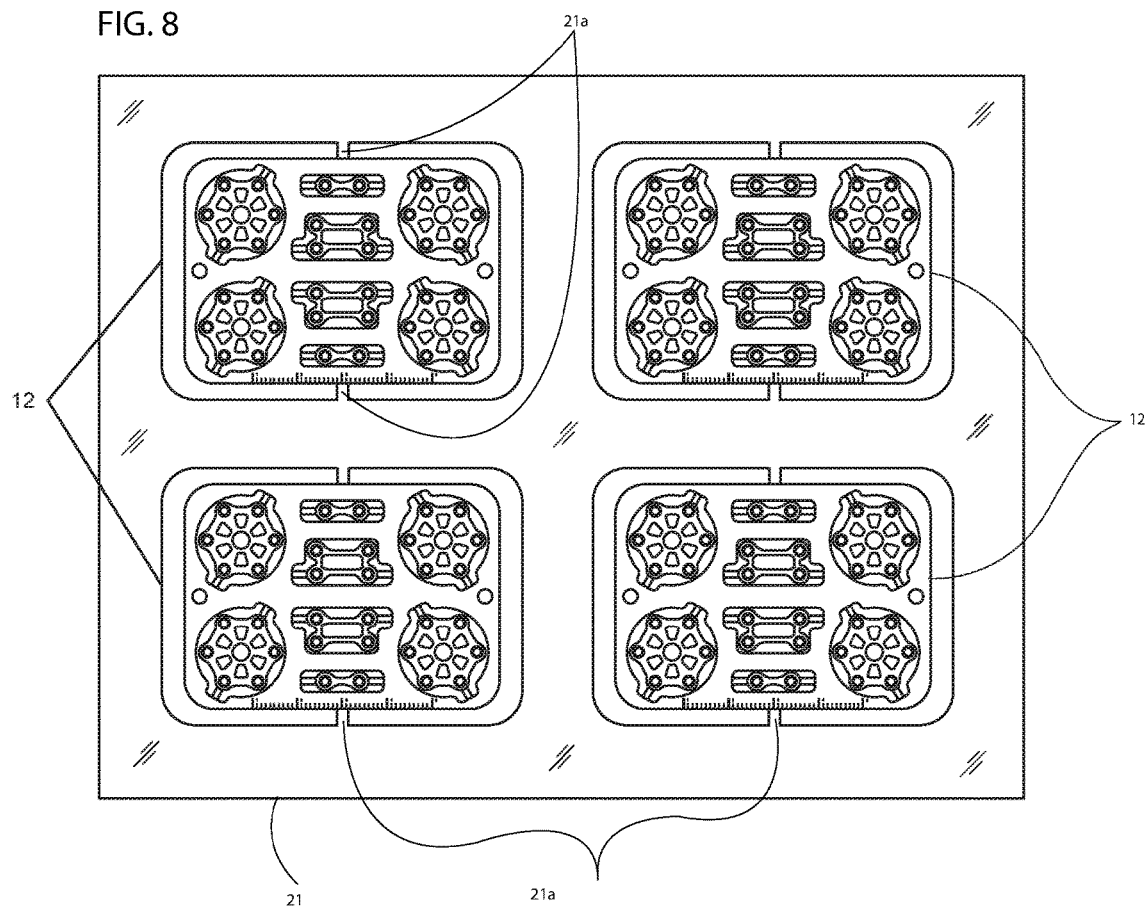
FIG. 8 is a plan view of another embodiment of the invention showing a plurality of card members provided in a single sheet of material.

In this regard, the card member 12 may be metallic, such as titanium, or a polymeric material, such as polyether ether ketone (PEEK). In one embodiment, the at least one or plurality of plates 14, 16 and 18 are integrally manufactured or molded into the card member 12 using conventional machining, etching, additive manufacturing, cutting, machining, chemical etching or the like. The card member 12 may also be molded into a single, one-piece or monolithic card member 12 having the at least one or plurality of plates 14, 16 and 18. Advantageously, the card member 12 with the at least one or plurality of plates 14, 16 and 18 features can be manufactured or molded in a single machining, molding or processing step. FIG. 8 also shows that a plurality of card members 12 could be provided in a single sheet of material 21. Note that each of the plurality of card members 12 may be broken from the single sheet of material 21 by manually breaking or cutting the webs 21a.

Returning back to FIGS. 1 and 2, it should be appreciated that while the at least one or plurality of plates 14, 16 and 18 may be affixed, adhered, integrally molded or machined or fastened to an interior area 34 of the card member 12, in a preferred embodiment, the card member 12 is machined, molded or processed to provide at least one or a plurality of webs, such as webs 14a, 16a and 18a, secure the at least one or plurality of plates 14, 16 and 18, respectively, to the card member 12. The at least one or plurality of webs 14a, 16a and 18a is adapted to permit a user to selectively remove at least one of the at least one or plurality of plates 14, 16 and 18 from the card member 12.

As illustrated in the sectional view in FIG. 3, note that the at least one or plurality of webs 14a, 16a and 18a comprise a thickness T2 that is less than the thickness T1 of the card member 12. Thus, it should be understood that the at least one or plurality of webs 14a, 16a and 18a are less thick than the thickness T1 to permit at least one of the at least one or plurality of plates 14, 16 and 18 to be separately or independently removed from the card member 12 either manually or by use of an instrument or tool, such as scissors or another cutting tool or instrument. In this regard, the card member 12 may be provided with at least one of the plurality of cut-out, etchedout, recessed or open areas 28, 30 and 32 associated with the at least one or plurality of webs 14a, 16a and 18a, respectively. Thus, the at least one of the plurality of cut-out, etched-out, recessed or open areas 28, 30 and 32 are adapted and sized to permit the ingress of a cutting instrument or tool (not shown) used for cutting the at least one or plurality of webs 14a, 16a and 18a.

Advantageously, it should be understood that in one illustrative embodiment the at least one or plurality of plates 14, 16 and 18 are integral or monolithic with the card member 12 and are integrally manufactured or monolithically formed or molded in the card member 12. The at least one or plurality of webs 14a, 16a and 18a are adapted to permit the user to selectively remove at least one of the at least one or plurality of plates 14, 16 and 18 from the card member 12 either manually or by using the cutting instrument or tool. While the card member 12 shows the at least one or plurality of webs 14a, 16a and 18a as integral and monolithic, the at least one or plurality of plates 14, 16 and 18 could be fastened to the card member 12 by other means, such as by an adhesive, weld, mating snap fit or the like.

In the illustration being described, the at least one or plurality of plates 14, 16 and 18 may comprise additional features, such as at least one or a plurality of screw holes, such as a hole 14b (FIG. 3) defined by a wall 14b1 in plate 14 or a hole 18b (FIG. 1) defined by a wall 18b1 in plate 18 or a hole 16b (FIG. 4) defined by a wall 16b1 in plate 16. Note, for example, with respect to the plate 16, that no apertures or windows are provided in the plate 16. However, the at least one or plurality of plates, such as plates 14 and 18, may comprise one or more walls, such as walls 14c1 and 18c1, that define one or more windows 14c and 18c in the plates 14 and 18, respectively.

The card member 12 may also be integrally or monolithically processed, machined, molded or formed to have other features, such as a plurality of aligners 50. In the illustration being described, the plurality of aligners 50 comprise at least one or a plurality of walls 52 that define at least one or a plurality of alignment holes 54, respectively. Advantageously, the at least one or a plurality of alignment holes 54 facilitate aligning, manufacturing, processing or molding the card member 12 or for use during a surgical procedure. For example, one or more tools (not shown) could be used in conjunction with the at least one or a plurality of alignment holes 54 to support the card member 12 so that a surgeon can align the at least one or plurality of plates 14, 16 and 18 in a desired position relative to a location where the at least one or plurality of plates 14, 16 and 18 will be mounted. Note in FIGS. 1 and 3, that other features may be provided on the card member 12 that are helpful during a surgical procedure. For example, an indicia 60 may be provided. In the illustration shown, the indicia 60 may be in the form of a ruler that a surgeon may use. In the example, the indicia 60 is in millimeters, but it could be in any desired unit of length or unit of measurement. The surgeon may use the card member 12 for measuring distances during a surgical procedure. Thus, the at least one or plurality of plates 14, 16 and 18 and indicia 60 are provided in one convenient card member 12, which is advantageous because it reduces or eliminates the need for separate instruments or components. One or more of the at least one or plurality of plates 14, 16 and 18 could comprise one or more handles 14e.

It should be understood that the card member 12 may comprise a holding area 62 (FIG. 1) that permits a surgeon to hold the card member 12 before and even during the surgical procedure. Thus, the surgeon may use the card member 12 as a holder and hold the at least one or plurality of plates 14, 16, and 18 in position during a surgical procedure, even as one or more bone screws (not shown) are received in the screw apertures, such as aperture or hole 14b.

As illustrated in FIG. 1, the card member 12 may be used to hold the at least one or plurality of plates 14, 16 and 18 in a predetermined position while one or more of the at least one or plurality of plates 14, 16 and 18 are mounted onto bone, after which the at least one or plurality of plates 14, 16 and 18 can be separated by, for example, cutting the at least one or plurality of webs 14a, 16a and 18a, respectively, near the intersection of the at least one or plurality of plates 14, 16 and 18 so that the at least one or plurality of plates 14, 16 and 18 can be separated and detached from the card member 12.

FIGS. 5-7 illustrate another embodiment wherein the card member 12 is provided with the plate 14. In this embodiment, like parts have the same part numbers as the embodiments in FIGS. 1-4. In this embodiment, the card member 12 is processed, etched, machined or molded such that one or more of the at least one or plurality of plates 14, 16 and 18 comprises a holder or handle 14e that is integrally or monolithically formed in the plate 14. In the illustration being described, the handle 14e is integrally or monolithically attached to the plate 14 with the web 14e1. Similar to the at least one or plurality of webs 14a, 16a and 18a mentioned earlier herein, the web 14e1 also comprises a thickness similar to the thickness T2, which is less than the thickness T1 of the card member 12 as illustrated in FIGS. 5 and 6. Thus, it should be understood that the integral placement handle 14e is adapted for use during a surgical procedure and can be separated from the at least one or plurality of plates 14, 16 and 18 after the at least one or plurality of plates 14, 16 and 18, for example, is mounted onto bone.

ADDITIONAL CONSIDERATIONS

It should be understood that the card member 12 and the at least one or plurality of plates 14, 16 and 18 have been shown as being generally planar in the illustrations and lying in a generally flat plane, but it should be understood that the card member 12 could be machined, molded or processed to have a non-planar shape, such as an arcuate, curved, cylindrical or other type of shape adapted to conform to the anatomical environment in which the at least one or plurality of plates 14, 16 and 18 are used. Also, each card member 12 may be of a material and thickness that permits it to be pliable and adaptable to the environment in which it is used.

Advantageously, this bone plating system or implant card 10 reduces or eliminates the need for traditional kits or drawers of plates, one dedicated to each size of plate. The embodiments being described herein permit the at least one or plurality of plates 14, 16 and 18 of different sizes that are provided on a single medium, such as the single card member 12, thereby reducing or eliminating the need for multiple-component kits. The bone plating system or implant card 10 provides a convenient, inexpensive, single-use component that contains the basic plating components needed for a specific procedure, such as a craniotomy procedure. For example, the typical plates for a craniotomy procedure may be embodied in a single card member 12, thereby providing a convenient system and means for providing the proper plates and adequate inventory thereof. Thus, the surgeon does not have to be concerned with selecting a plurality of different cards because all the appropriate plates for a surgical procedure are provided in a single card.

One advantageous and unique feature of the embodiments being described is that bone plating system or implant card 10 can be provided and manufactured during a single operation, such as a single machining, processing, etching, molding or chemical etching operation which provides cost savings.

While the bone plating system or implant card 10 described herein comprises the dimensions mentioned earlier, it should be appreciated that a card member 12 could be provided with smaller or larger dimensions of thickness (T1, T2), length (L) or width (W). Such characteristics may be determined in part by the size or shape of the at least one or plurality of plates 14, 16 and 18 to be provided in the card member 12, the number of plates and types of plates used during a particular surgical procedure, a weight of the card member 12, the anatomical environment in which the card member 12 will be used or the like.

This invention, including all embodiments shown and described herein, could be used alone or together and/or in combination with one or more of the features covered by one or more of the claims set forth herein, including but not limited to one or more of the features or steps mentioned in the Summary of the Invention and the claims.

While the system, apparatus and method herein described constitute preferred embodiments of this invention, it is to be understood that the invention is not limited to this precise system, apparatus and method, and that changes may be made therein without departing from the scope of the invention which is defined in the appended claims.

What is claimed is:

1. A bone plating system comprising:
   a card member;
   said card member having a plurality of plate members integrally manufactured in or monolithically formed in said card member;
   wherein said card member is generally planar and defines a generally planar support, each of said plurality of plate members being coupled to, manufactured or formed in said generally planar support via at least one web that is adapted to permit a user to selectively remove each of said plurality of plate members from said generally planar support;
   wherein said card member has a holding area adapted to permit a user to position or align at least one of said plurality of plate members during a surgical operation and prior to said at least one said plurality of plate members being separated from said card member; and
   each of said plurality of plate members being substantially surrounded by at least one wall in said card member.

2. The bone plating system as recited in claim 1 wherein said card member comprises a plurality of plate members integrally manufactured in or monolithically formed in said card member.

3. The bone plating system as recited in claim 1 wherein said card member comprises a plurality of plate members that are each at least one of a different shape or a different size.

4. The bone plating system as recited in claim 1 wherein said plurality of plate members being coupled to said generally planar support via a plurality of webs that are adapted to permit a user to selectively remove at least one of the plurality of plate members from said generally planar support.

5. The bone plating system as recited in claim 2 wherein said plurality of plate members each comprise a plurality of screw holes adapted to receive a bone screw.

6. The bone plating system as recited in claim 4 wherein each of said plurality of webs has a thickness that is less than a thickness of said generally planar support to facilitate a user removing said at least one of the plurality of plate members from said generally planar support.

7. The bone plating system as recited in claim 4 wherein said generally planar support comprises a plurality of recesses associated with said plurality of webs, respectively, said plurality of recesses being adapted and sized to permit ingress of a cutting instrument used for cutting said plurality of webs.

8. The bone plating system as recited in claim 2 wherein at least one of said plurality of plate members comprises at least one integral placement handle.

9. The bone plating system as recited in claim 2 wherein said card member is generally planar and metallic, said plurality of plate members are provided in said card member by at least one of machining, etching, or cutting.

10. The bone plating system as recited in claim 2 wherein said card member is made of a molded polymer material, said plurality of plate members being molded in said card member.

11. The bone plating system as recited in claim 1 wherein said card member comprises an indicia.

12. The bone plating system as recited in claim 11, wherein said indicia comprises a ruler indicia.

13. The bone plating system as recited in claim 1 wherein said card member comprises at least one aligner for aligning said card member during a processing operation.

14. The bone plating system as recited in claim 13 wherein said at least one aligner comprises a plurality of alignment apertures.

15. The bone plating system as recited in claim 2 wherein said card member comprises a plurality of edges that cooperate to define an interior area in said card member, said plurality of plate members being generally located in said interior area.

16. The bone plating system as recited in claim 2 wherein said plurality of plate members in said card member are made by a single processing operation.

17. The bone plating system as recited in claim 1 wherein said card member is less than about ⅛ inch thick.

18. The bone plating system as recited in claim 1 wherein said card member comprises a length less than about 4 inches, a width less than about 3 inches, and a thickness of less than about ⅛ inch.

19. An implant card comprising:
   a card member;
   said card member comprising a plurality of plates adapted to be detached or removed from said card member for use on a patient;
   wherein said card member is generally planar and defines a generally planar support;
   said plurality of plates being coupled to or formed to said generally planar support via at least one web that is adapted to permit a user to selectively remove said plurality of plates from said generally planar support;
   wherein said card member has a holding area adapted to permit a user to position or align said plurality of plates during a surgical operation and prior to said plurality of plates being separated from said card member;
   each of said plurality of plates being surrounded by at least one wall that substantially encloses said each of said plurality of plates.

20. The implant card as recited in claim 19 wherein said card member and said plurality of plates are a single, integral or monolithic construction.

21. The implant card as recited in claim 20 wherein said card member is metallic or polymeric and adapted to allow a selection of at least one of said plurality of plates to be selectively removed either before or during a surgical procedure.

22. The implant card as recited in claim 20 wherein said card member comprises a support member, said plurality of plates are integrally or monolithically attached to said support member using at least one web.

23. The implant card as recited in claim 22 wherein said at least one web comprises a thickness that is less than a thickness of said support member.

24. The implant card as recited in claim 23 wherein said card member comprises recesses generally located at a point or intersection where said at least one web interfaces the card member to permit ingress of a cutting tool.

25. The implant card as recited in claim 20 wherein at least one of said plurality of plates has a shape or size that is different from another of said plurality of plates.

26. The implant card as recited in claim 20 wherein said plurality of plates comprises at least one first group of plates and at least one second group of plates, said at least one first group of plates comprises a size or shape that is different from a size and shape of said at least one second group of plates.

27. The implant card as recited in claim 20 wherein said plurality of plates can be separately or independently removed from said card member manually or with a hand tool.

28. The implant card as recited in claim 20 wherein said card member has at least one aligner adapted to facilitate manufacturing, machining or processing the card member.

29. The implant card as recited in claim 28 wherein said at least one aligner comprises a plurality of holes.

30. The implant card as recited in claim 19 wherein said card member comprises a ruler indicia.

31. The implant card as recited in claim 19 wherein said card member comprises a holding area for allowing a user to hold said implant card substantially simultaneously when at least one of said plurality of plates is being mounted to bone.

32. The implant card as recited in claim 19 wherein at least one of said plurality of plates comprises an integral placement handle adapted for use during a surgical procedure and that can be separated from said at least one of said plurality of plates.

33. The bone plating system as recited in claim 1 wherein a plurality of card members are integrally formed or molded in a single sheet of material.

\* \* \* \* \*

UNITED STATES PATENT AND TRADEMARK OFFICE
CERTIFICATE OF CORRECTION

PATENT NO. : 10,285,770 B2
APPLICATION NO. : 15/049642
DATED : May 14, 2019
INVENTOR(S) : David Louis Kirschman It is certified that error appears in the above-identified patent and that said Letters Patent is hereby corrected as shown below:

In the Claims

Column 9, Line 45, Claim 1, insert --of-- after "one".

Signed and Sealed this
Ninth Day of July, 2019

Andrei Iancu
*Director of the United States Patent and Trademark Office*